United States Patent [19]

Drake

[11] Patent Number: 4,602,119

[45] Date of Patent: Jul. 22, 1986

[54] DEHYDRATION OF ALCOHOLS EMPLOYING A CARBOXYLIC ACID TREATED CATALYST

[75] Inventor: Charles A. Drake, Nowata, Okla.

[73] Assignee: Phillips Petroleum Company, Bartlesville, Okla.

[21] Appl. No.: 604,712

[22] Filed: Apr. 27, 1984

[51] Int. Cl.$^4$ .................................................. C07C 1/24
[52] U.S. Cl. ..................................... 585/640; 585/639; 502/355
[58] Field of Search ................. 585/639, 640; 502/355

[56] References Cited

U.S. PATENT DOCUMENTS

| | | | |
|---|---|---|---|
| 1,913,938 | 6/1933 | Metzger et al. | 585/640 |
| 3,251,896 | 5/1966 | Navarre | 502/355 |
| 3,686,286 | 8/1972 | Ahn et al. | 585/640 |
| 3,903,251 | 9/1975 | Sieg et al. | 44/56 |
| 3,932,306 | 1/1976 | Rona | 502/168 |
| 4,234,752 | 11/1980 | Wu et al. | 585/640 |
| 4,306,106 | 12/1981 | Kerr et al. | 502/77 |
| 4,387,085 | 6/1983 | Fanelli et al. | 423/628 |
| 4,398,051 | 8/1983 | Araki et al. | 585/639 |
| 4,423,270 | 12/1983 | Pearson | 585/639 |
| 4,447,669 | 5/1984 | Hamon et al. | 585/639 |
| 4,529,827 | 7/1985 | Drake | 585/640 |

*Primary Examiner*—John Doll
*Assistant Examiner*—Anthony McFarlane
*Attorney, Agent, or Firm*—A. W. Umphlett

[57] ABSTRACT

An improved process for dehydrating alcohols in which the catalyst used in the dehydration process is activated using an organic carboxylic acid.

10 Claims, No Drawings

DEHYDRATION OF ALCOHOLS EMPLOYING A CARBOXYLIC ACID TREATED CATALYST

This invention relates to the dehydration of alcohols. It further relates to a process for the dehydration of alcohols. In particular it relates to a pretreatment of a dehydration catalyst used in the dehydration of alcohols.

BACKGROUND

The dehydration of alcohols to produce olefins is known. This process is important because the olefins produced from the dehydration are used in further processes. For example, 2-alkyl-1-alkenes such as 2-methyl-1-butene and 4-methyl-1-pentene are well known polyolefin modifiers and there is a large market for these compounds.

Principally the dehydration reaction is one involving the removal of the elements of water from the alcohol. In some cases a single olefin will result upon the dehydration; in others a mixture of olefins will be obtained. For instance, the dehydration of 2-methyl-2-butanol can produce at least two olefins, 2-methyl-1-butene, which as mentioned before is a desirable product, and 2-methyl-2-butene, a less desirable product. The formation of other products occurs through isomerization.

It is the object of this invention to maximize the production of desired olefin products, while minimizing the production of undesirable olefin products through isomerization.

It is a general object of this invention to dehydrate an alcohol. It is a further object of this invention to provide a process for the dehydration of alcohols. A specific object of this invention is to provide a pretreatment of the dehydration catalyst used in the dehydration of alcohols that increase the selectivity and conversion rate of the alcohol, minimizing the isomerization of the olefin. Other objects will become apparent from the following disclosure.

SUMMARY OF THE INVENTION

According to the instant invention an alumina dehydration catalyst is treated with an organic carboxylic acid to provide an improvement in the activity and selectivity of the alumina catalyst for the dehydration of alcohols to olefins.

DETAILED DESCRIPTION OF THE INVENTION

Suitable organic carboxylic acids have 1-10 carbon atoms per molecule, 1-4 carboxyl groups per molecule, and can be aliphatic, alicyclic or aromatic carboxylic acids. Furthermore, halogen (preferably fluorine or chlorine)-substituted organic carboxylic acids are also suitable within the above description. Examples of suitable organic carboxylic acids include formic acid, acetic acid, propanoic acid, hexanoic acid, decanoic acid, oxalic acid, malonic acid, succinic acid, adipic acid, benzoic acid, cyclopentanecarboxylic acid, phthalic acid, 1,2,3-propanetricarboxylic acid, 1,3,5-benzenetricarboxylic acid, 1,2,4,5-benzenetetracarboxylic acid, chloroacetic acid, trichloroacetic acid, trifluoroacetic acid, bromoacetic acid, 4-chlorocyclohexanecarboxylic acid, 4-chlorobenzoic acid and 2,4,6-tribromobenzoic acid.

The amount of organic carboxylic acid employed in the treatment of the alumina can be broadly from about 0.005 g to about 0.5 g of acid per gram of alumina, but preferably from about 0.01 g to about 0.1 g per gram of alumina.

It is convenient and usually preferred to utilize a solution or dispersion of the organic carboxylic acid in a diluent to contact the alumina catalyst. Said diluent should be substantially inert to the alumina and the organic carboxylic under the conditions employed. Suitable diluents include water; hydrocarbons such as pentane, hexane, toluene, and cyclohexane; esters such as ethyl acetate, methyl benzoate, and butyl acetate. The concentration of organic carboxylic acid in said diluent is not critical and can be chosen for convenience in handling and economic efficiency. For those organic carboxylic acids which are normally liquid under the treating conditions it is also possible to utilize such acids in the absence of a diluent.

The temperature employed in the treatment of the alumina with the organic carboxylic acid is broadly from 0° to 100° C., preferably from 15° to 35° C. The time of treatment can range from a few minutes to several hours, preferably from about 15 minutes to about one hour.

The treatment of the alumina according to this invention can be conducted by merely allowing the alumina to "soak" in the presence of the organic carboxylic acid (including diluent, if any) with or without gentle agitation of the mixture. At the conclusion of the treatment the liquid phase is decanted and the treated alumina dried at about 100° C. until a substantially constant weight is observed.

The alumina dehydration catalysts treated according to the instant invention are those conventionally employed in alcohol dehydration reactions. Typically, these are finely divided aluminas having a minimum content of $Al_2O_3$ of about 90% by wt. These aluminas generally have surface areas in the range of 20–600 $m^2/g$, preferably 100–300 $m^2/g$. In terms of U.S. Standard Sieve mesh size they generally range from 6–40 mesh, preferably from 8–20 mesh. Suitable aluminas can be in the gamma or chi form or can be a mixture such as boehmite (aluminum oxide-hydroxide)/chi-alumina composition.

Alcohols which are dehydrated to the corresponding olefins by means of this invention generally include the straight chain or branched-chain alcohols containing from 2 to about 20 carbon atoms per molecule. These can contain primary, secondary, or tertiary alcohol groups. This invention yields especially beneficial results with branched-chain alcohols containing from 4 to about 10 carbon atoms.

Alcohols which can be used in the process of this invention include ethanol, 1-propanol, 2-methyl-2-propanol, 2-methyl-1-butanol, 3-methyl-1-butanol, 3-methyl-2-butanol, 2,4-dimethyl-1-hexanol, 1-octanol, 2,11-dimethyl-2-dodecanol, 1-hexadecanol, 1-eicosanol, and the like.

Olefins produced by the process of this invention generally correspond to the starting alcohol from which elements of water have been removed. For example, the dehydration of 2-methyl-1-butanol will result, generally, in 2-methyl-1-butene. This invention minimizes isomerization which in this example would produce 2-methyl-2-butene and the like.

The inert carrier gas employed in this invention can be any gas, or any inert gas, which is unreactive at existing reaction conditions, such as nitrogen, helium, argon, and the like, or mixtures thereof.

It is preferable to employ the desirable alcohol and inert carrier gas in the absence of any additional solvent or diluent. It is within the scope of this invention to employ any solvent in the dehydration reaction which will not adversely affect the reaction.

The alcohol generally is added to the reactor under desired reaction conditions at a rate of from about 0.1 to 20 weight hourly space velocity, and preferably 0.5 to 2 weight hourly space velocity.

The flow of inert carrier gas has not been found to be critical in obtaining good results according to this invention. In general, the flow rate can vary from about 3 liters per hour to about 66 liters per hour, however, an optimum rate of conversion and selectivity occur between 40 liters per hour and 50 liters per hour.

Generally, temperatures in the range of from about 200° to 550° C. are suitable for the desired dehydration reaction to occur. It is currently preferable, however, to employ temperatures in the range of 300°–450° C. Due to the exothermicity of the dehydration reaction, it may be desirable to provide external means of cooling for the desired temperature control.

The pressures under which the desired dehydration reaction will occur can vary widely, for example, from about 50 to about 3,500 kPa. It is generally preferable, however, to maintain some pressure and pressures in the range of 100–700 kPa are now contemplated as being desirable.

The reaction mixture can be separated readily into desired products, by-products, and unreacted starting materials using conventional methods such as solvent extraction, fractional distillation, fractional condensation, etc. An especially suitable means for isolating desired product involves the passage of gaseous reactor effluent into successively cooler zones, for example, 50° C. followed by 0° C. followed by −70° C. Most of the water and unreacted starting materials condense at the higher temperatures, while desired olefins are recovered at the lower temperatures.

EXAMPLE I

As a control run 2-methyl-1-butanol was subjected to a dehydration reaction employing a commercially available alumina designated F-1 obtained from Aluminum Company of America. F-1 alumina is characterized by the following typical properties:

Composition:
 $Al_2O_3$: 92 wt. %
 $Na_2O$: 0.9 wt. %
 $Fe_2O_3$: 0.08 wt. %
 $SiO_2$: 0.09 wt. %
Loss on Ignition (1100° C.): 6.5 wt. %.
Form: Granular.
Surface Area: 210 m$^2$/g.

A $\frac{1}{2}'' \times 20''$ stainless steel tubular reactor was charged with 38 g of the above F1 alumina. The temperature was brought up to 400° C. under nitrogen flowing at 3.3 L/hr. The alcohol was then fed to the reaction zone at a rate of 36 mL/hr. Effluent from the reaction zone was collected and analyzed by gas chromatography.

Under these conditions a feedstock conversion of 81% was obtained with an 81% selectivity to 2-methyl-1-butene.

EXAMPLE II

In an inventive run, about 100 g of F1 alumina described in Example I was soaked in about 100 mL of 2% of wt. aqueous acetic acid for about one hr. The liquid was decanted and the alumina dried at 100° C. until constant weight was reached. The reaction apparatus of Example I was charged with 38 g of the treated catalyst. The reaction zone was heated under flowing nitrogen at 3.3 L/hr and the alcohol was fed to the reaction zone at 36 mL/hr. The reaction was conducted at different temperatures with the reaction effluent being collected and analyzed as before. The results are presented in Table I below.

TABLE I

| Run No. | Temp. °C. | Conversion, wt. % | Selectivity, wt. % to 2-MB-1[a] |
|---|---|---|---|
| 1 | 300 | no reaction | — |
| 2 | 320 | 5 | 99 |
| 3 | 340 | 15 | 99 |
| 4 | 360 | 33 | 94 |
| 5 | 380 | 52 | 89 |
| 6 | 400 | 91 | 86 |

[a] 2-MB-1 = 2-methyl-1-butene

Comparison of the results in Example I with Run 6 of Table I shows that the catalyst treatment according to this invention provided a significantly higher conversion of feedstock with increased selectivity to the desired olefin, 2-methyl-1-butene.

I claim:
1. A process for dehydrating an alcohol to an olefin comprising contacting said alcohol, under dehydration reaction conditions of temperature and pressure with an alumina dehydration catalyst, where said catalyst has been subjected to a soaking treatment with an organic carboxylic acid for a time sufficient to provide a treated dehydration catalyst of improved selectivity and rate of conversion of alcohol as compared to untreated catalyst.

2. A process according to claim 1 where said organic carboxylic acid is an aliphatic, alicyclic or aromatic carboxylic acid having from 1 to about 10 carbon atoms and from 1 to about 4 carboxyl groups per molecule.

3. A process according to claim 2 where said organic carboxylic acid is a halogen-substituted organic carboxylic acid.

4. A process according to claim 1 where said organic carbocylic acid is acetic acid.

5. A process according to claim 1 where the amount of organic carboxylic acid employed is about 0.005 g to about 0.5 g of said carboxylic acid per gram of alumina.

6. A process according to claim 5 where the amount of organic carboxylic acid ranges from about 0.01 g to about 0.1 g of said carboxylic acid per gram of alumina.

7. A process according to claim 1 where an inert diluent is also present when said catalyst is subjected to said soaking treatment with said acid.

8. A process according to claim 1 where said soaking treatment is from about 15 minutes to about one hour.

9. A process according to claim 1 where said soaked catalyst is further treated by drying until constant weight of said soaked catalyst is observed.

10. A process according to claim 1 where said alumina dehydration catalyst has a minimum alumina content of about 90% by weight.

* * * * *